(12) United States Patent
Park et al.

(10) Patent No.: US 9,942,232 B2
(45) Date of Patent: Apr. 10, 2018

(54) USER CONTROL OF DATA DE-IDENTIFICATION

(71) Applicant: Verily Life Sciences LLC, Mountain View, CA (US)

(72) Inventors: Brian Taewon Park, San Francisco, CA (US); Russell Norman Mirov, Los Altos, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 0 days.

(21) Appl. No.: 14/325,715

(22) Filed: Jul. 8, 2014

(65) Prior Publication Data

US 2016/0014129 A1  Jan. 14, 2016

(51) Int. Cl.
G06F 17/00 (2006.01)
H04L 29/06 (2006.01)
A61B 5/00 (2006.01)

(52) U.S. Cl.
CPC ............ H04L 63/10 (2013.01); A61B 5/0022 (2013.01); A61B 5/6801 (2013.01); A61B 5/681 (2013.01); A61B 2562/08 (2013.01)

(58) Field of Classification Search
None
See application file for complete search history.

(56) References Cited

U.S. PATENT DOCUMENTS

| | | |
|---|---|---|
| 7,214,190 B1 | 5/2007 | Wilson |
| 7,701,580 B2 | 4/2010 | Bassler et al. |
| 7,763,856 B2 | 7/2010 | Kiesel et al. |

(Continued)

FOREIGN PATENT DOCUMENTS

| | | |
|---|---|---|
| WO | 2013188838 A2 | 12/2013 |
| WO | 2014-040175 A1 | 3/2014 |

(Continued)

OTHER PUBLICATIONS

Manuel Arruebo, Mónica Valladares, and África González-Fernández, Antibody-Conjugated Nanoparticles for Biomedical Applications, Journal of Nanomaterials, vol. 2009 (2009), Article ID 439389, 24 pages (available at http://dx.doi.org/10.1155/2009/439389).

(Continued)

*Primary Examiner* — Esther B Henderson

(74) *Attorney, Agent, or Firm* — Christensen O'Connor Johnson Kindness PLLC

(57) ABSTRACT

A method for transmitting, storing and sharing data collected by a wearable device is provided. In one example, data related to one or more measurements obtained by the wearable device configured to be mounted to a body surface of a wearer is received in addition to an input by the wearer of the device. The input selects at least one identification rule that determines whether or how the wearer is identified in connection with the data from the wearable device. The data is stored in a database based, at least in part, on the at least one identification rule. The input from the wearer may also select at least one permission rule that determines whether third parties can access the data from the wearable device. A third party may be required to provide payment for access to or use of the data according to the at least one permission rule.

14 Claims, 6 Drawing Sheets

(56) References Cited

U.S. PATENT DOCUMENTS

| | | | |
|---|---|---|---|
| 7,817,254 | B2 | 10/2010 | Hegyi et al. |
| 7,817,276 | B2 | 10/2010 | Kiesel et al. |
| 7,844,314 | B2 | 11/2010 | Al-Ali |
| 7,894,068 | B2 | 2/2011 | Bassler |
| 8,153,949 | B2 | 4/2012 | Kiesel et al. |
| 8,323,188 | B2 | 12/2012 | Tran |
| 8,344,731 | B2 | 1/2013 | Lee |
| 8,368,402 | B2 | 2/2013 | Lee et al. |
| 8,635,087 | B1 | 1/2014 | Igoe |
| 8,803,366 | B2 | 8/2014 | Proud |
| 2003/0009593 | A1* | 1/2003 | Apte .............. G06Q 20/383 709/245 |
| 2004/0139204 | A1* | 7/2004 | Ergezinger ...... G06Q 30/0601 709/229 |
| 2004/0259270 | A1 | 12/2004 | Wolf |
| 2005/0054907 | A1 | 3/2005 | Page et al. |
| 2005/0203792 | A1 | 9/2005 | Kuppe et al. |
| 2007/0255122 | A1 | 11/2007 | Vol et al. |
| 2008/0094926 | A1* | 4/2008 | Neel ............... G06F 21/6218 365/201 |
| 2008/0120707 | A1* | 5/2008 | Ramia .............. H04L 63/0861 726/5 |
| 2010/0049010 | A1 | 2/2010 | Goldreich |
| 2011/0028803 | A1 | 2/2011 | Ollmar |
| 2011/0117028 | A1 | 5/2011 | Zharov |
| 2011/0314555 | A1 | 12/2011 | Horvitz et al. |
| 2012/0198368 | A1* | 8/2012 | Bornheimer ............ G06F 8/38 715/763 |
| 2013/0006718 | A1 | 1/2013 | Nielsen et al. |
| 2013/0097664 | A1 | 4/2013 | Herz et al. |
| 2013/0190903 | A1 | 7/2013 | Balakrishnan et al. |
| 2014/0032259 | A1 | 1/2014 | LaFever et al. |
| 2014/0121476 | A1 | 5/2014 | Tran et al. |
| 2014/0129253 | A1 | 5/2014 | Hanina et al. |
| 2014/0133656 | A1 | 5/2014 | Wurster et al. |
| 2014/0135592 | A1 | 5/2014 | Ohnemus et al. |
| 2014/0188874 | A1 | 7/2014 | Stivoric et al. |
| 2014/0300490 | A1* | 10/2014 | Kotz .................. A61B 5/0028 340/870.3 |
| 2014/0343371 | A1 | 11/2014 | Sowers, II et al. |
| 2015/0035644 | A1 | 2/2015 | June |
| 2015/0125832 | A1 | 5/2015 | Tran |
| 2015/0199010 | A1* | 7/2015 | Coleman .............. A61B 5/0006 345/156 |
| 2015/0351695 | A1 | 12/2015 | Cronin |
| 2016/0008632 | A1 | 1/2016 | Wetmore et al. |

FOREIGN PATENT DOCUMENTS

| | | |
|---|---|---|
| WO | 2015033152 A2 | 3/2015 |
| WO | 2015094188 A1 | 6/2015 |

OTHER PUBLICATIONS

Shao et al, "Magnetic nanoparticles for biomedical NMR-based diagnostics," Beilstein Journal of Nanotechnology, 2010, 1, 142-154.

Liu et al, "Magnetic resonance monitoring of focused ultrasound/magnetic nanoparticle targeting delivery of therapeutic agents to the brain," PNAS Early Edition, 2010, pp. 1-6.

Search Report and Written Opinion for PCT/US2015/039307 dated Oct. 30 2015.

\* cited by examiner

USER CONTROL OF DATA DE-IDENTIFICATION

BACKGROUND

Unless otherwise indicated herein, the materials described in this section are not prior art to the claims in this application and are not admitted to be prior art by inclusion in this section.

A number of scientific methods have been developed in the medical field to evaluate a person's health state. A person's health state may, for example, be evaluated based on the measurement of one or more physiological parameters, such as blood pressure, pulse rate, skin temperature, or galvanic skin response (GSR). In a typical scenario, these measurements may be taken in the home or a health-care setting by using several discreet devices or sensors and, in some cases, by drawing blood or other bodily fluid. For most people, the measurements or blood tests are performed infrequently, and changes in a physiological parameter, which may be relevant to health state, may not be identified, if at all, until the next measurement is performed.

In another example, these parameters may be more frequently or continuously measured, and other health-related information obtained, by a wearable device. The device, which may be provided as a wrist-mounted device, may include one or more sensors for detecting or measuring one or more physiological parameters. For example, a wrist-mounted device may include optical sensors for heart rate and blood oxygen saturation ($SpO_2$) monitoring, a thermistor for measuring skin temperature, and a GSR sensor for measuring skin resistance. At least some of the physiological parameter information may be obtained by detecting the presence, absence and/or concentration of one or more analytes in the body. The wearable device may further include or be in communication with other sensors such as accelerometers, inertial measurement units (IMU), infrared sensors, ultrasonic sensors, optical sensors, gyroscopes, magnetometers, odometers, pedometers, pressure sensors, strain gauges, GPS devices, a clock, etc.

SUMMARY

A wearable device may collect physiological data from a wearer of the device and transmit that data to the cloud or other remote server or device. A wearer of the device may control the level of identifying information associated with that data. In some examples, a wearer's data may be de-identified prior to storage in or retrieval from the cloud. Further, a wearer may control access to and use of her data. A wearer may also set controls such that a third party may be required to pay a wearer of the device in order to access and/or use her data. The collected data may be stored in the cloud based on the identification and/or access permissions rules set by the wearer of the device.

Some embodiments of the present disclosure provide a method including: (1) receiving, by a server from a wearable device, data related to one or more measurements obtained by the wearable device, wherein the wearable device is configured to be mounted to a body surface of a wearer; (2) receiving, by the server, an input from the wearer, wherein the input selects at least one identification rule that determines whether or how the wearer is identified in connection with the data from the wearable device; and (3) storing, by the server, the data in a database based, at least in part, on the at least one identification rule.

Further embodiments of the present disclosure provide a method including: (1) receiving, by a server from a wearable device, data related to one or more measurements obtained by the wearable device, wherein the wearable device is configured to be mounted to a body surface of a wearer; (2) receiving, by the server, an input from the wearer, wherein the input selects at least one permission rule that determines whether third parties can access the data from the wearable device; and (3) permitting, by the server, a third party to access the data based, at least in part, on the at least one permission rule.

Still further embodiments of the present disclosure provide a method including: (1) receiving, by a server from a wearable device, data related to one or more measurements obtained by the wearable device, wherein the wearable device is configured to be mounted to a body surface of a wearer; (2) receiving, by the server, an express identifier associated with the data, wherein the express identifier reveals the identity of the wearer; (3) replacing, by the server, the express identifier with a synthetic identifier, wherein the synthetic identifier does not reveal the identity of the wearer; (4) establishing a relationship between the express identifier and the synthetic identifier; (5) establishing one or more groups based, at least in part, on at least one rule; and (6) storing, by the server, the data from the wearable device in the database, such that the stored data includes an indication that all or part of the data is associated with the one or more groups.

These as well as other aspects, advantages, and alternatives, will become apparent to those of ordinary skill in the art by reading the following detailed description, with reference where appropriate to the accompanying drawings.

DETAILED DESCRIPTION

Figure 1:
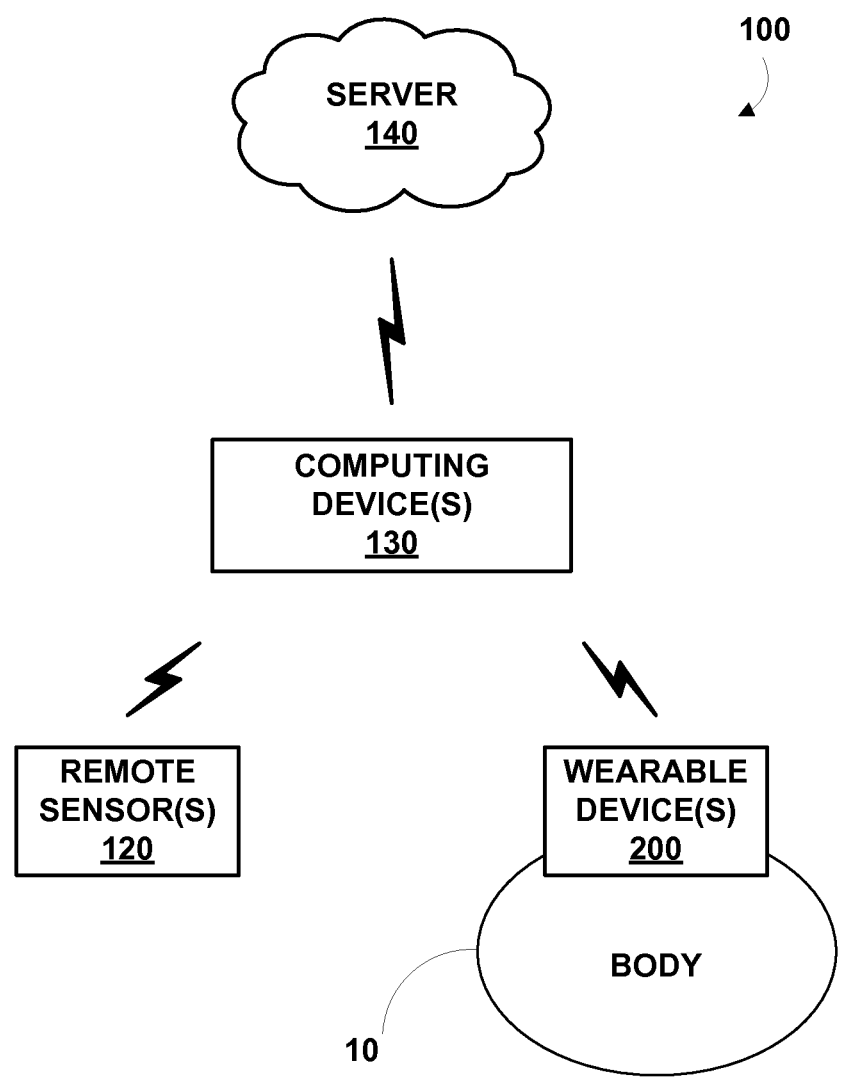
FIG. 1 is a block diagram of an example system that includes a wearable device, according to an example embodiment.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

I. Overview

A wearable device may collect physiological and other data from a wearer of the device and transmit that data to the cloud or other remote server or device. For example, the wearable device may detect one or more physiological parameters, such as heart rate, blood pressure, respiration rate, blood oxygen saturation (SpO$_2$), skin temperature, skin color, galvanic skin response (GSR), muscle movement, eye movement, blinking, and speech. Some physiological data may also be obtained by non-invasively detecting and/or measuring one or more analytes present in blood, saliva, tear fluid, or other body fluid of the wearer of the device. The one or more analytes could include enzymes, reagents, hormones, proteins, viruses, bacteria, cells or other molecules, such as carbohydrates, e.g., glucose. Further, the wearable device, or a device associated with the wearable device, may collect motion-related data, such as the wearer's speed of travel, altitude, acceleration, cadence of movement, intensity of movement, direction of travel, orientation, gravitational force, inertia, and rotation. This data may be collected by sensors such as accelerometers, IMUs, proximity sensors, microphones, gyroscopes, magnetometers, optical sensors, ultrasonic sensors, odometers, and pedometers. Additionally, the wearable device may collect certain contextual data, such as a wearer's location, ambient light intensity, ambient temperature, time of day, a wearer's mode of travel, and a type of activity a wearer is participating in. Accordingly, the wearable device may include a location-tracking sensor (e.g., a GPS device), a light intensity sensor, a thermometer, and a clock. A wearer's personal or demographic data, such as sex, race, region or country of origin, age, weight, height, employment, medical history, etc., may also be collected and transmitted to the cloud.

The term "wearable device," as used in this disclosure, refers to any device that is capable of being worn or mounted at, on, in or in proximity to a body surface, such as a wrist, ankle, waist, chest, ear, eye, head or other body part. As such, the wearable device can collect data while in contact with or proximate to the body. For example, the wearable device can be configured to be part of a contact lens, a wristwatch, a head-mountable device, an orally-mountable device such as a retainer or orthodontic braces, a headband, a pair of eyeglasses, jewelry (e.g., earrings, ring, bracelet), a head cover such as a hat or cap, a belt, an earpiece, other clothing (e.g., a scarf), and/or other devices. Further, the wearable device may be mounted directly to a portion of the body with an adhesive substrate, for example, in the form of a patch, or may be implanted in the body, such as in the skin or another organ.

In some examples, the data described above may be collected directly by sensors integrated on the wearable device. Alternatively, or additionally, some or all of the data described above may be collected by sensors placed on other portions of a wearer's body or in communication with the body, other computing devices remote to the wearable device (such as a remote device having location tracking and internet capabilities, e.g. a smartphone, tablet or head-mountable device), or by manual input by the wearer. For example, the wearer may manually input when she is exercising, eating, work, or sleeping, the type of activity she is engaged in (running, typing, walking, climbing), her self-evaluated physical, health or mental state or mood (e.g., hungry, tired, headache, anxious, etc.), among other things. Data may also be collected from applications on other computing devices linked with the wearable device such as an electronic calendar, social media applications, restaurant reservation applications, travel applications, etc.

Data collected from or relating to each wearer of a device may be associated with one or more express identifiers that reveal the identity of the wearer, such as the wearer's name, address, or social security number. In some examples, a wearer's data may be transferred to and stored in the cloud with an express identifier, which may be used to organize all data collected from or related to a particular user. When data is extracted from the cloud, this direct association to the wearer's identity may be maintained with the data, such that a person accessing this data would be able to identify the particular wearer from the data. This type of data may be referred to as "identified" data.

Additionally or alternatively, upon transfer and storage in the cloud, a user's data may be "de-identified," such that a wearer's express identifier is altered or removed and replaced with a synthetic identifier that does not reveal the identity of a particular user. In a further example, data may be de-identified and associated with the synthetic identifier upon extraction from the cloud by, for example, a third party. This synthetic identifier, while not revealing the identity of a particular wearer to someone viewing the data, may be used, for example by a system administrator, to trace data back to the wearer from which it came. This is in contrast to anonymized data which cannot be linked back to its origin. De-identified data from many wearers or data across time from a single wearer may be aggregated in the cloud. This aggregated data may be useful for identifying correlations across populations of wearers or to see trends over time. The system may also be configured to use the synthetic identifier to identify a particular wearer's data from an aggregated set of data of a population of wearers.

The system may allow wearers of the device to control third-party access to data transmitted to and stored in the cloud, including both identified and de-identified data. For example, a wearer may set rules governing whether certain data points or data sets will be transferred to the cloud in an "identified" or "de-identified" mode. The "mode" rules may be set based on the type of data, results of the data, transferee, etc. In some cases, these rules may act to automatically set the transfer mode. If a wearer has not set a rule governing a certain type of data, the wearer may be prompted to select the mode upon each data transfer. Further, the system may be configured to automatically set the mode based on statistics or thresholds. Instances may occur where a wearer's identity may be determined from de-identified data because, for example, the wearer is the only person in a geographical area from which data is being collected. In this case, the system may notify the user such that appropriate measures may be taken to protect the wearer's identity, if so desired.

In the identified mode, a wearer may set up permissions or rules which would allow certain third parties to access all or part of the wearer's identified data. For example, a wearer may elect to share her identified data with a spouse, friend, parent, doctor, caretaker, or other person. These permissions may be organized as a mapping table that associates an express identifier of each wearer with identifiers of those third parties that have been granted access, the category of data they have been given access to (e.g., heart rate data, exercise data, sleep data, location data, etc.) and the type of access the third party has been granted. Access controls may be organized concentrically, e.g., no access, read access, edit access, access to transfer ownership (data for minor owned by parent until wearer turns 18, then ownership reverts back to user). Accordingly, data may be stored in the cloud such that the source of the data (e.g., which wearer) and the type of data (e.g., heart rate data from optical heart rate sensor).

A wearer may be provided with control over her de-identified data. For example, a wearer may opt-out from sharing her de-identified data with third parties. In other examples, a wearer may allow her de-identified data to be accessed by third parties without restriction. For example, aggregated de-identified data may be available to a system administrator and other third parties. In further examples, a wearer may set certain rules restricting third-party use of and/or access to her de-identified data. The wearer may specify that only certain third parties may access and use her de-identified data and that only certain de-identified data may be made accessible.

Additionally, rules may be set in the system such that a third party may use or access a wearer's data in exchange for a monetary payment, such as a micropayment or other benefit having a monetary value (e.g., member benefit points, coupons, discounts, gift cards, etc.). A micropayment, in some examples, may be a relatively small amount of money, including a fraction of a cent, a few dollars or over twenty dollars. In some cases, the payment may be made to a wearer of the device and/or to a system administrator. The system administrator may, for example, charge a fee for a third party to access databases or aggregate data. Monetizing access to a wearer's data may also provide incentive for wearers to share data with or permit access by third parties. The wearer of the device may specify instances in which a payment is required for a third-party to receive access to her data. For example, the wearer may set rules for the types of data she will share, with whom she will share it, and the price of such access and use. The wearer may also specifically elect to share certain data, in an identified or de-identified mode, with a specified third party for a specified purpose. For example, the wearer may elect to participate in a clinical trial in which the wearer will share certain data with a third party in exchange for a payment.

In some cases, a wearer's data may acquire value over time. For example, long term exercise, eating or sleep data may be of value to a third party (individual data points or daily data of this type may not hold value). Similarly, certain data may become valuable after a milestone. For example, the past or future data of a wearer may become valuable after the wearer experiences a heart attack or is diagnosed with a medical condition. Accordingly, while a wearer may not require payment for access to her data initially, she may set a rule requiring payment at a point in time where the data is more valuable. Further, the wearer (or the system administrator) may also require a post-access or use payment if a third party ultimately determines that the data is valuable and desires to use that data in a certain manner, for example, if the third party ultimately uses the data as part of a study. In cases of aggregate or de-identified data, the wearer's synthetic identifier may be used to trace a data set or data points back to that wearer so that payment may be made.

The term "medical condition" as used herein should be understood broadly to include any disease, illness, disorder, injury, condition or impairment—e.g., physiologic, psychological, cardiac, vascular, orthopedic, visual, speech, or hearing—or any situation affecting the health of the wearer of the device or requiring medical attention. A "medical condition" may also include a situation where a physiological parameter falls outside of a range, regimen or recommendation set by an individual, her physician, a clinician or a nutritionist. For example, a "medical condition" may be indicated when an individual consumes more than the daily recommended calories or consumes food having a high level of fat or sugars.

It should be understood that the above embodiments, and other embodiments described herein, are provided for explanatory purposes, and are not intended to be limiting.

II. Example Wearable Devices and Systems

As shown in FIG. 1, a system 100 may include one or more wearable devices 200 configured to be mounted to or worn on, in or in proximity to a body 10, one or more remote sensors 120, and one or more computing devices 130 all in communication with a server 140. Remote sensor 120 may be any sensor not provided directly on the wearable device 200. For example, a remote sensor 120 may be mounted to a wearer's bicycle or car, on the wearer's desk, near a wearer's bed or outside of a wearer's home. Computing device 130 may be any device having computing or internet capabilities, including a smartphone or tablet, a personal computer, a mobile or cellular telephone, or a web-based application. In one embodiment, the one or more remote sensors 120 and wearable devices 200 indirectly communicate with server 140 via computing device 130. In other embodiments, the wearable device 200, remote sensor 120 and computing device 130 may all directly communicate with the server 140.

The device 200, remote sensor 120 and/or computing device 130 may be capable of collecting, detecting or measuring a plurality of parameters from or associated with a person wearing the device, such as physiological, motion, contextual, and personal parameters. As will be described further below, these parameters may be detected on one or more of the wearable device 200, the remote sensors 120 and the computing devices 130. Physiological parameters may include heart rate, blood pressure, respiration rate, blood oxygen saturation ($SpO_2$), skin temperature, skin color, galvanic skin response (GSR), perspiration, muscle movement, eye movement, blinking, speech and analyte concentration. Motion-related parameters, such as the wearer's speed of travel, altitude, acceleration, cadence of movement, intensity of movement, direction of travel, orientation, gravitational force, inertia, and rotation. Contextual parameters, such as a wearer's location, ambient light intensity, ambient temperature, humidity, allergen levels, pollution, time of day, a wearer's mode of travel, and a type of activity a wearer is participating in, may also be collected. A wearer's "location" could be any location with respect to a 2-dimensional or 3-dimensional coordinate system (e.g., a location with respect to X, Y and Z axes) or with respect to a cartographic location description (e.g., a street address), and may further include a global position (e.g., latitude, longitude and elevation), a hyper-local position (such as a location within a home or building), and/or any position at any level of resolution therebetween. Personal parameters may include sex, race, region or country of origin, age, weight, height, employment, occupation, and medical history, etc.

The wearable device 200, remote sensor(s) 120 and computing device(s) 130 may be configured to transmit data, such as collected physiological, motion, contextual and personal parameter data via a communication interface over one or more communication networks to the remote server 140. The communication interface may include any means for the transfer of data, including both wired and wireless communications, such as a universal serial bus (USB) interface, a secure digital (SD) card interface, a plain old telephone service (POTS) network, a cellular network, a fiber network and a data network. In one embodiment, the communication interface includes a wireless transceiver for sending and receiving communications to and from the server. The wearable device 200, remote sensor(s) 120 and computing device(s) 130 may also be configured to communicate with one another via any communication means.

Further, the computing device 130 may be capable of accessing information on the internet, a wearer's electronic calendar, or from a software application. The computing device 130 may collect data regarding the wearer's schedule, appointments, and planned travel. In some cases, the computing device 130 may also access the internet or other software applications, such as those operating on a wearer's smartphone. For example, the computing device 130 may access an application to determine the temperature, weather and environmental conditions at the wearer's location. All of this collected data may be transmitted to the remote server 140.

In addition to receiving data from the wearable device 200, remote sensor(s) 120 and computing device(s) 130, the server may also be configured to gather and/or receive additional information from other sources. For example, the server may be configured to regularly receive viral illness or food poisoning outbreak data from the Centers for Disease Control (CDC) and weather, pollution and allergen data from the National Weather Service. Further, the server may be configured to receive data regarding a wearer's health state or existing medical conditions from a hospital or physician. Such information may be used in the server's decision-making process, such as recognizing correlations and in generating recommendations.

One or more of the wearable device 200, remote sensor 120 or computing device 130 may also be capable of receiving an input from a wearer and transmitting that input to the server 140. For example, the wearer may input one or more rules or an indication of her "state." As will be described further below, the wearable device 200 may include an interface 280 with one or more controls 284 via which the wearer may provide an input. A wearer may also provide an input on a computing device 130, such as a smartphone, tablet or laptop computer.

Figure 2:
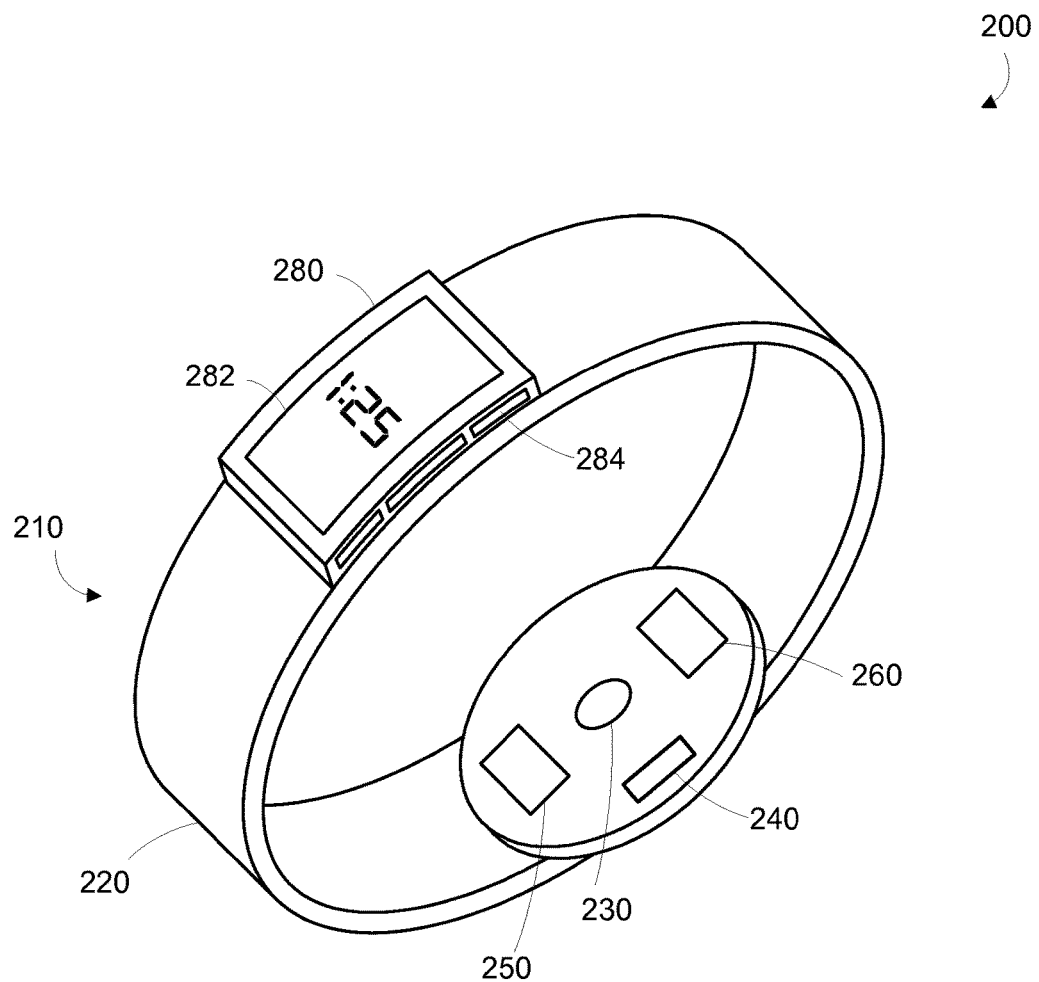
FIG. 2 illustrates an example of a wearable device.

Turning to FIG. 2, the wearable device 200 may be provided as any device configured to be mounted in, on or adjacent to a body surface. In the example shown in FIG. 2, the wearable device 200 is a wrist-mountable device 210, but many other forms are contemplated. The device may be placed in close proximity to the skin or tissue, but need not be touching or in intimate contact therewith. A mount 220, such as a belt, wristband, ankle band, necklace, or adhesive substrate, etc. can be provided to mount the device at, on or in proximity to the body surface.

The wearable device 200 may include one or more sensors 230 for collecting data from or associated with a wearer of the device 210, a transceiver 240 for transmitting collected data to a remote server or device, a processor 250 and a memory 260. Transceiver 240 may include a wireless transceiver with an antenna that is capable of sending and receiving information to and from a remote source, such as a server 140. Memory 260 is a non-transitory computer-readable medium that can include, without limitation, magnetic disks, optical disks, organic memory, and/or any other volatile (e.g. RAM) or non-volatile (e.g. ROM) storage system readable by the processor 250. The memory 260 can include a data storage to store indications of data, such as sensor readings, program settings (e.g., to adjust behavior of the wearable device 200), user inputs (e.g., from a user interface on the device 200 or communicated from a remote device), etc. The memory 260 can also include program instructions for execution by the processor 250 to cause the device 200 to perform operations specified by the instructions. The operations could include any of the methods described herein. Example processor(s) 250 include, but are not limited to, CPUs, Graphics Processing Units (GPUs), digital signal processors (DSPs), application specific integrated circuits (ASICs).

The sensors 230 may include any device for collecting, detecting or measuring one or more physiological, motion, contextual or personal parameters. Sensors for detecting and measuring physiological parameters may include, but are not limited to, one or more of an optical (e.g., CMOS, CCD, photodiode), acoustic (e.g., piezoelectric, piezoceramic), electrochemical (voltage, impedance), resistive, thermal, mechanical (e.g., pressure, strain), magnetic, or electromagnetic (e.g., magnetic resonance) sensor. In particular, the wearable device 100 may include sensors such as a thermometer and a GSR sensor for sensing temperature and skin resistance, respectively, and a light emitting source and a detector for sensing blood pressure. Some physiological data may also be obtained by non-invasively detecting and/or measuring one or more analytes present in blood, saliva, tear fluid, or other body fluid of the wearer of the device. The one or more analytes could include enzymes, reagents, hormones, proteins, viruses, bacteria, cells or other molecules, such as carbohydrates, e.g., glucose. Analyte detection and measurement may be enabled through several possible mechanisms, including electrochemical reactions, change in impedance, voltage, or current etc. across a working electrode, and/or interaction with a targeted bioreceptor. For example, analytes in a body fluid may be detected or measured with one or more electrochemical sensors configured to cause an analyte to undergo an electrochemical reaction (e.g., a reduction and/or oxidation reaction) at a working electrode, one or more biosensors configured to detect an interaction of the target analyte with a bioreceptor sensitive to that analyte (such as proteins, enzymes, reagents, nucleic acids, phages, lectins, antibodies, aptamers, etc.), and one or more impedimetric biosensors configured to measure analyte concentrations at the surface of an electrode sensor by measuring change in impedance across the electrode, etc. Other detection and quantification systems and schemes are contemplated for implementation of the analyte sensor system.

Contextual parameters may be detected from, for example, a location-tracking sensor (e.g., a GPS or other positioning device), a light intensity sensor, a thermometer, a microphone and a clock. Motion data may be collected by sensors such as accelerometers, IMUs, proximity sensors, microphones, gyroscopes, magnetometers, optical sensors, ultrasonic sensors, odometers, and pedometers. These sensors and their components may be miniaturized so that the wearable device may be worn on the body without significantly interfering with the wearer's usual activities. Additionally or alternatively, these sensors may be provided on or as part of a remote sensor 120 or a computing device 130.

The wearable device 200 may also include an interface 280 via which the wearer of the device may receive one or more recommendations or alerts generated either from a remote server 140, remote computing device 130, or from the processor 250 provided on the device. The alerts could be any indication that can be noticed by the person wearing the wearable device. For example, the alert could include a visual component (e.g., textual or graphical information on a display), an auditory component (e.g., an alarm sound), and/or tactile component (e.g., a vibration). Further, the interface 280 may include a display 282 where a visual indication of the alert or recommendation may be displayed. The display 282 may further be configured to provide an indication of the detected or collected physiological, motion, contextual or personal parameters, for instance, the wearer's heart rate. In embodiments where the wearable device is not capable of supporting an interface 280, alerts and recommendations may be provided to the wearer on computing device 130. The interface 280 may also include one or more controls 284 via which a user may input an indication of her state, or, in some cases a rule related to the data detected by the wearable device. The controls 284 may allow a user to select and input one or more options regarding, for example, how her data is to be stored by the server (e.g., one or more identification rules) and how her data may be accessed by third parties (e.g., one or more permission rules). These options may be displayed on the interface 280, for example, in lists or menus that the user may navigate using the controls 284. These inputs by the user may be transmitted to the server 140.

In other examples, the wearable device 200 may be provided as or include an eye-mountable device, a head mountable device (HMD) or an orally-mountable device. An eye-mountable device may, in some examples, take the form of a vision correction and/or cosmetic contact lens, having a concave surface suitable to fit over a corneal surface of an eye and an opposing convex surface that does not interfere with eyelid motion while the device is mounted to the eye. The eye-mountable device may include at least one sensor provided on a surface of or embedded in the lens material for collecting data. In one example, the sensor can be an amperometric electrochemical sensor for sensing one or more analytes present in tear fluid.

An HMD may generally be any display device that is capable of being worn on the head and places a display in front of one or both eyes of the wearer. Such displays may occupy a wearer's entire field of view, or occupy only a portion of a wearer's field of view. Further, head-mounted displays may vary in size, taking a smaller form such as a glasses-style display or a larger form such as a helmet or eyeglasses, for example. The HMD may include one or more sensors positioned thereon that may contact or be in close proximity to the body of the wearer. The sensor may include a gyroscope, an accelerometer, a magnetometer, a light sensor, an infrared sensor, and/or a microphone for collecting data from or associated with a wearer. Other sensing devices may be included in addition or in the alternative to the sensors that are specifically identified herein.

An orally mountable device may be any device that is capable of being mounted, affixed, implanted or otherwise worn in the mouth, such as on, in or in proximity to a tooth, the tongue, a cheek, the palate, the lips, the upper or lower jaw, the gums, or other surface in the mouth. For example, the device 200 can be realized in a plurality of forms including, but not limited to, a crown, a retainer, dentures, orthodontic braces, dental implant, intra-tooth device, veneer, intradental device, mucosal implant, sublingual implant, gingivae implant, frenulum implant, or the like. The orally-mountable device may include one or more sensors to detect and/or measure analyte concentrations in substances in the mouth, including food, drink and saliva. Sensor(s) that measure light, temperature, blood pressure, pulse rate, respiration rate, air flow, and/or physiological parameters other than analyte concentration(s) can also be included.

Figure 3:
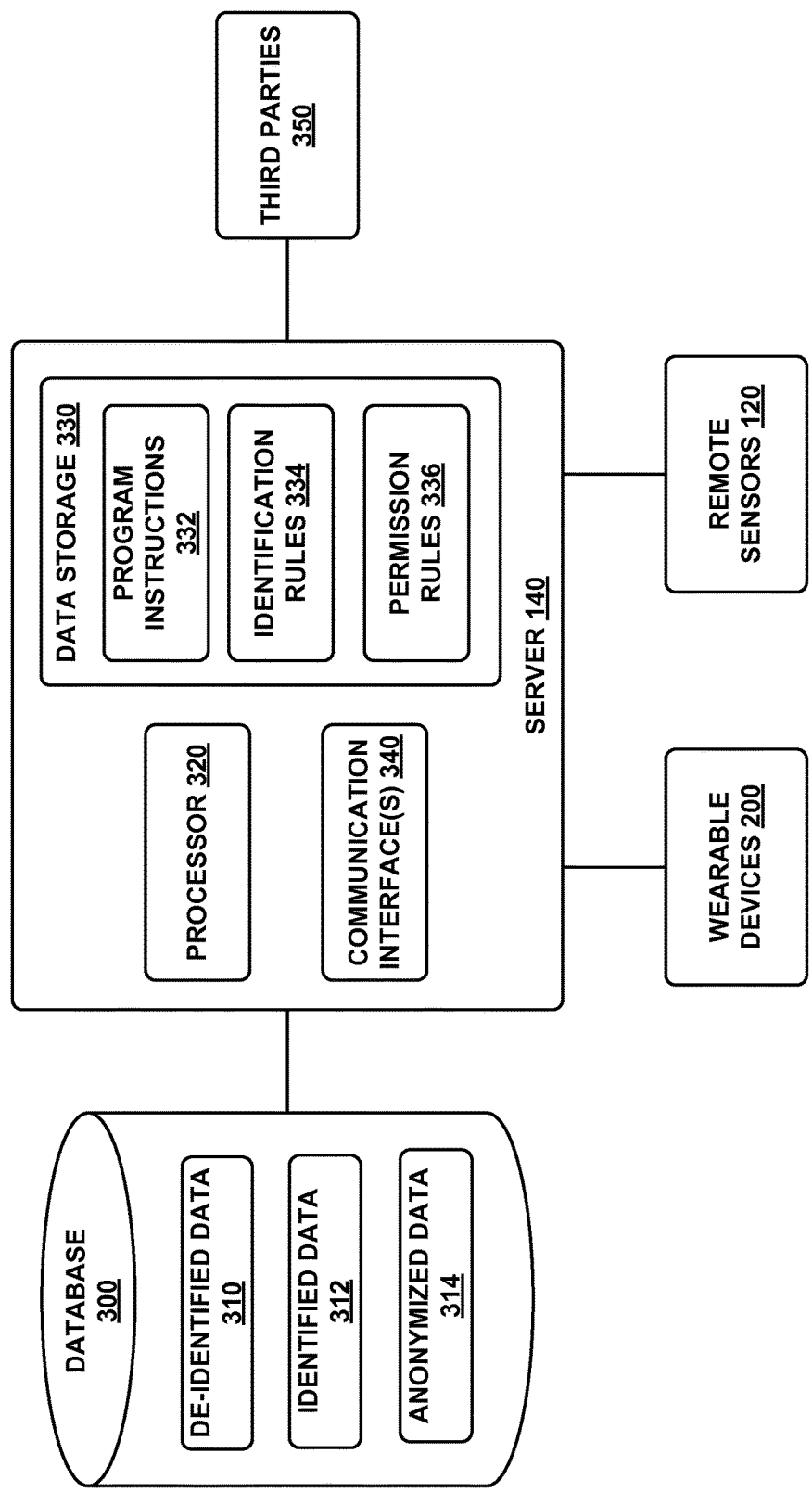
FIG. 3 is a schematic diagram of an example system.

FIG. 3 schematically illustrates the flow of data collected by one or more wearable devices 200 and/or remote sensors 120 between the server 140, a database 300 and one or more third parties 350. The server may include a processor 320, a data storage 330, and a communication interface 340 for communicating with the remote sensors 120 and wearable devices 200 over one or more communication networks. The communication interface 340 may include any means for the transfer of data, including both wired and wireless communications, such as a universal serial bus (USB) interface, a secure digital (SD) card interface, a plain old telephone service (POTS) network, a cellular network, a fiber network and a data network. In one embodiment, the communication interface includes a wireless transceiver for sending and receiving communications from and to the server 140.

Data storage 330 is a non-transitory computer-readable medium that can include, without limitation, magnetic disks, optical disks, organic memory, and/or any other volatile (e.g. RAM) or non-volatile (e.g. ROM) storage system readable by the processor 320. The data storage 330 can store data, such as sensor readings, and one or more identification rules 334 and permission rules 336 based, at least in part, on a user input. The data storage 330 can also include program instructions 332 for execution by the processor 320 to cause the server 140 to perform operations specified by the instructions. Those operations could involve any of the methods described herein. Example processor(s) 320 include, but are not limited to, CPUs, Graphics Processing Units (GPUs), digital signal processors (DSPs), application specific integrated circuits (ASICs).

Physiological, motion, contextual and personal parameter data transmitted from the wearable device(s) 200 and/or the remote sensor(s) 120 to the server via a communication interface over one or more communication networks to the remote server 140 may be stored in the database 200 according to the one or more identification rules 334 residing in the data storage. The identification rules 334 may be based on an input by the wearer of the wearable device 200 received by the server 14, and may govern how the wearer wants her data to be stored. For example, the wearer may input that she wants certain data stored as de-identified data 310, identified data 312, or anonymized data 314. The identification rules may be based on the type of collected data (e.g. location data, heart rate data, nutrition data), the types of third parties 350 who may be provided access to the data, the type of use to which a third party 350 indicates the data will be put, or any other characteristics of the data.

Third parties 350 may be provided access to the data stored on the database 300 based on one or more permission rules 336 residing in the data storage 330. The permission rules 336 may be based on an input by the wearer of a wearable device 200 received by the server 140 and may govern how, to whom, and for what purposes the wearer will permit access to her stored data. For example, the permission rules 336 may specify that certain third parties may have no access to the wearer's data. The permission rules 336 may also govern which data stored in the database 300 may be accessed by which third-parties, for which purposes. Further, the permission rules 336 may govern the identification mode in which the data will be accessed—de-identified, identified or anonymized.

III. Example Methods

Figure 4:
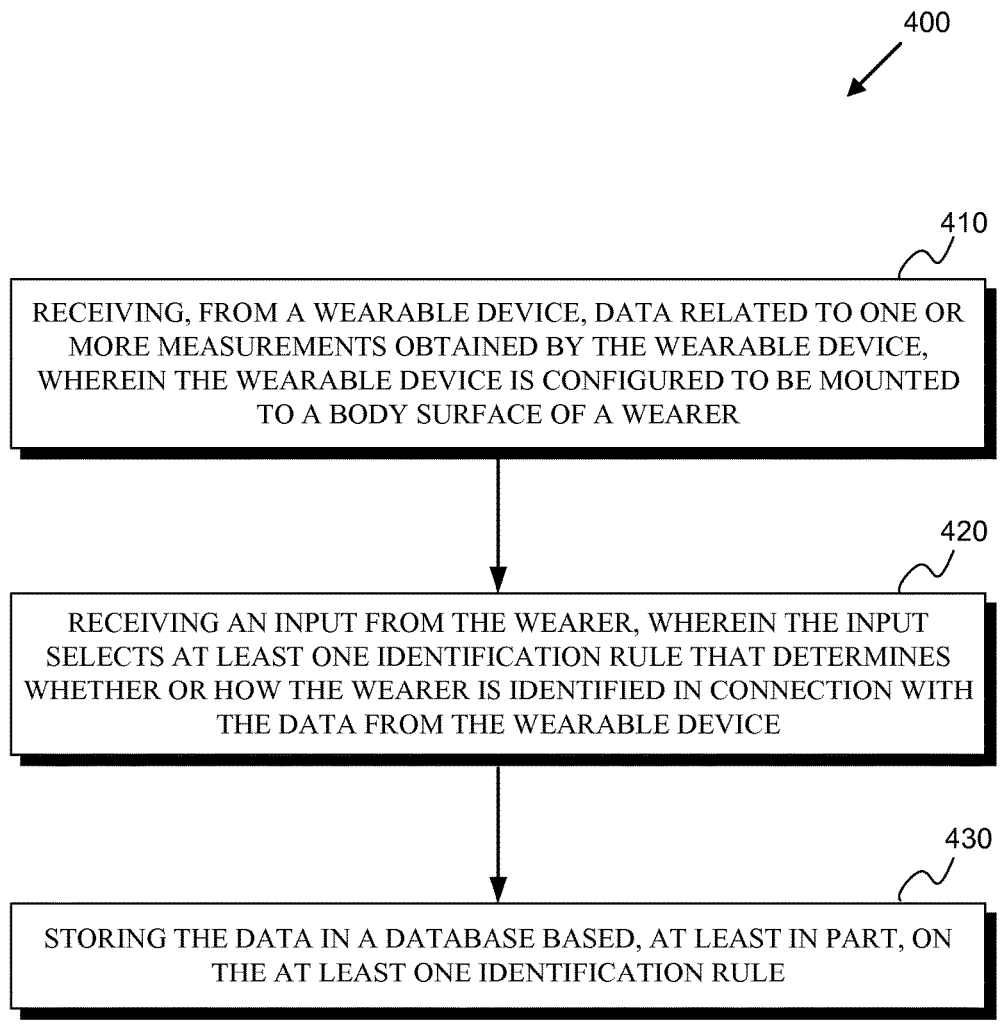
FIG. 4 is a flow chart of an example method, according to an example embodiment.

FIG. 4 is a flowchart of a method 400 for handling data detected from a wearer of a wearable device. As described above, a wearable device 200, configured to be mounted to a body surface, may detect physiological data from a wearer of the device. Data related to one or more measurements obtained by the wearable device may then be received by, for example, a processor on the wearable device 200, a remote computing device 130 or a remote server 140, such as a cloud computing network (410). An input by the wearer of the device may also be received, for example, by the server 140 (420). The input may be received directly by the server 140, or may be input by the wearer into the wearable device 200, a remote sensor 120, or a computing device 130, such as a smartphone or laptop computer and transmitted to the server 140. While embodiments of the foregoing methods are described herein as being carried out on the server 140, it is contemplated that the methods may be carried out by a processor on the wearable device 200, remote sensor 120 or computing device 130.

The input may comprise a selection by the wearer of at least one identification rule that determines whether or how the wearer is identified in connection with the data from the wearable device. In one example, the identification rule may dictate that the data is associated with an express identifier that reveals the identity of the wearer. In one example, an express identifier may be the wearer's birthdate, social security number, home address, mobile phone number, drivers' license number, etc. In another example, the identification rule may dictate that the data is associated with a synthetic identifier that does not reveal the identity of the wearer. The synthetic identifier may be a combination of letters, numbers or other characters that does not directly identify the wearer. Each wearer may be assigned a synthetic identifier. The relationship between the identity of the wearer and the synthetic identifier may be stored in a secure database. The data received by, for example, the server 140 may be stored in a database based on the identification rule (430). In some examples, the data is stored in the database under the wearer's synthetic identifier or the wearer's express identifier.

The identification rules may also determine how the wearer is identified, based on the type of data. For example, the rule may govern which type of identifier is to be associated with certain types of data. For example, the wearer may input that she wants all of her physiological data to be de-identified. Thus, all of the wearer's physiological data will be stored in the database associated with her synthetic identifier. The identification rule may also determine whether or how the wearer is identified based on permitted third-party access to the data. For example, the wearer may input that certain third parties are permitted to access all or certain types of the wearer's de-identified data. The types of data indicated by the wearer would be stored in the database associated with her synthetic identifier indicating the third parties with permitted access. Similarly, the wearer may input that certain third parties are permitted to access all or certain types of the wearer's identified data. The types of data indicated by the wearer would be stored in the database associated with her express identifier indicating the third parties with permitted access. Further, the identification rule may also determine whether or how the wearer is identified based, at least in part, on intended third-party use of the data. The wearer may input that a third party may access and use her identified or de-identified data, but only for specified purposes. For example, the wearer may input that her insurance company may access and use her activity or exercise data associated with her express identifier, but only for purposes of evaluating her insurance coverage or premiums.

In addition to physiological data, the system may be configured to receive motion data, contextual data, and personal data associated with the wearer of a wearable device. As described above, these types of data may be detected or collected by one or more of a wearable device 200, a computing device 130, a remote sensor 120 or the server 140. In some examples, the motion and contextual data may be detected synchronously with the physiological data. The wearer may input similar identification rules for all of these types of data.

Figure 5:
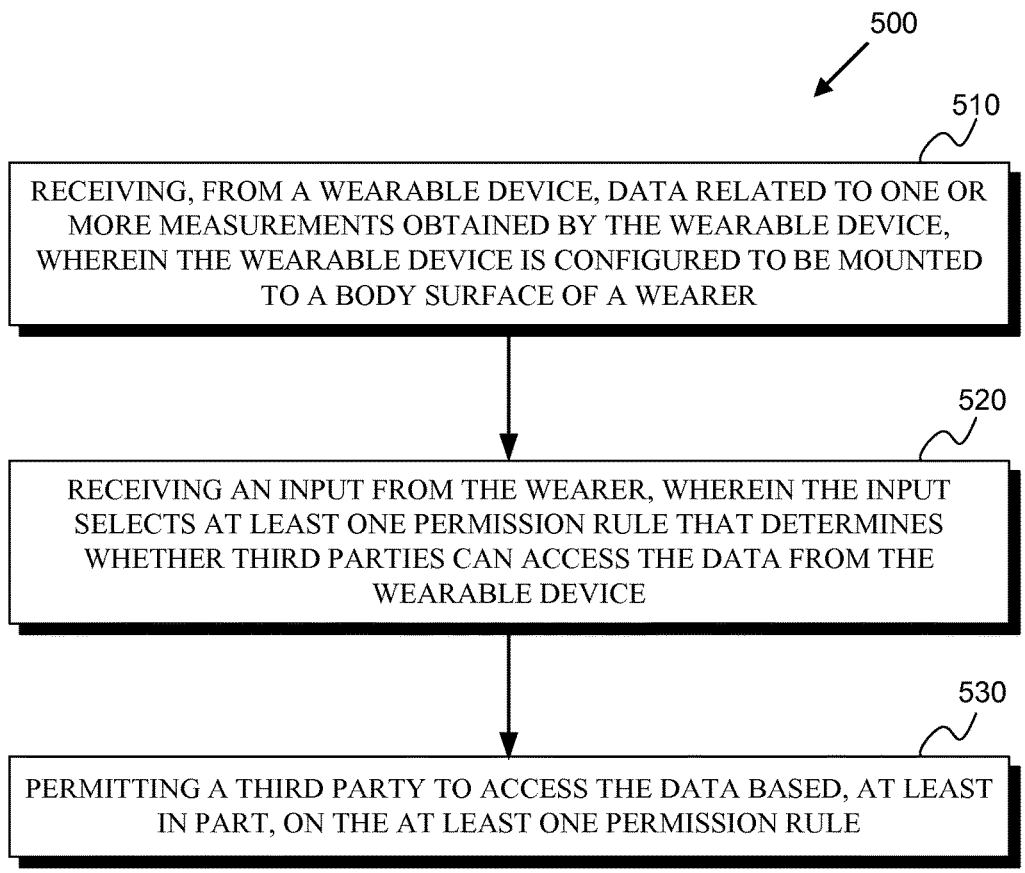
FIG. 5 is a flow chart of an example method, according to an example embodiment.

FIG. 5 is a flowchart of another method 500 for handling data detected from a wearer of a wearable device. Data related to one or more measurements obtained by a wearable device is received, for example, by the remote server 140 which may, in some examples, be the cloud (510). An input is received from the wearer that selects at least one permission rule (520). The permission rule determines whether third parties can access the data from the wearable device. For example, the permission rule may determine the types of data that may be accessed, if at all, by certain third parties. In other examples, the permission rule may govern the type of third party that may access all or part of the wearer's data. The permission rule may determine that a wearer's parent or guardian may have access to all of the wearer's data, whereas a wearer's soccer coach may only be permitted to access a wearer's activity data during certain days and times. A third party is then permitted to access the data based, at least in part, on the at least one permission rule (530). In some examples, the permission rule may direct that the wearer must receive a payment, such as a micropayment, from a third party to access the data. The permission rule may also direct that the wearer receive a micropayment for increments of data. For example, the wearer may set a rule that a third party must pay the wearer $4 for each day of the wearer's activity data for which it wants access.

Figure 6:
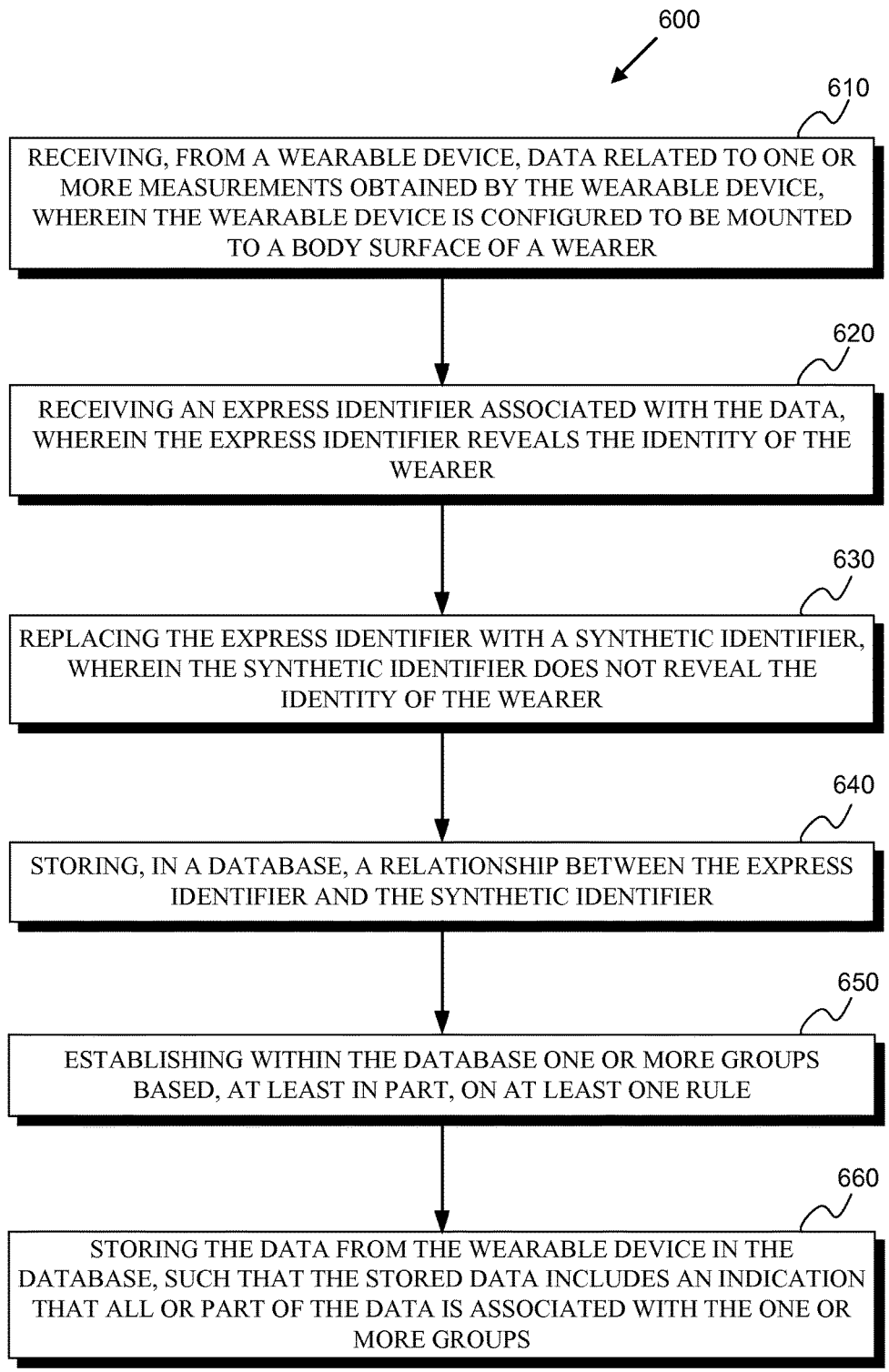
FIG. 6 is a flow chart of an example method, according to an example embodiment.

FIG. 6 is a flowchart of another method 600 for handling data detected from a wearer of a wearable device. Data related to one or more measurements obtained by the wearable device may then be received by, for example, a processor on the wearable device 200, a remote computing device 130 or a remote server 140, such as a cloud computing network (610). An express identifier associated with the data may also be received (620). The express identifier, which reveals the identity of the wearer, is replaced with a synthetic identifier that does not reveal the identity of the wearer (630). A relationship between the express identifier and the synthetic identifier is stored in a database (640). One or more groups may be established within the database, based, at least in part, on at least one rule (650) and the data is stored in the database with an indication that all or part of the data is associated with the one or more groups (660). The groups may be categories according to which the data is organized and stored. For example, the categories may be types of collected data (e.g., location data, activity data, sleep data, etc.), the identification mode of the data (e.g., identified, de-identified), the permitted uses of the data, and the third-parties permitted to access and/or use the data.

The at least one rule, which may be a permission rule, that determines whether third parties can access the data, or an identification rule, that determines how a user's data is identified, may be based on an input by the wearer. The permission rule may also specify one or more conditions that a third party must meet in order to access and/or use the data. For example, the third party may be required to pay the user for access or use of the data. In another example, the third party must specify that the data will be used for only certain purposes as specified by the wearer.

It will be readily understood that the aspects of the present disclosure, as generally described herein, and illustrated in the figures, can be arranged, substituted, combined, separated, and designed in a wide variety of different configurations, all of which are explicitly contemplated herein. While various aspects and embodiments have been disclosed herein, other aspects and embodiments will be apparent to those skilled in the art.

Example methods and systems are described above. It should be understood that the words "example" and "exemplary" are used herein to mean "serving as an example, instance, or illustration." Any embodiment or feature described herein as being an "example" or "exemplary" is not necessarily to be construed as preferred or advantageous over other embodiments or features. Reference is made herein to the accompanying figures, which form a part thereof. In the figures, similar symbols typically identify similar components, unless context dictates otherwise. Other embodiments may be utilized, and other changes may be made, without departing from the spirit or scope of the subject matter presented herein. The various aspects and embodiments disclosed herein are for purposes of illustration and are not intended to be limiting, with the true scope and spirit being indicated by the following claims.

What is claimed is:
1. A method, comprising:
receiving, by a server, data related to one or more measurements obtained by a wearable device, wherein the wearable device is mounted to a body surface of a wearer;
receiving, by the server, a selection of at least one permission rule;

determining, by the server, whether a third party can access the data from the wearable device based on the at least one permission rule;
receiving, by the server, a selection of at least one identification rule;
determining, by the server based on a third party use of the data, the at least one identification rule and the at least one permission rule, a type of one or more identifiers to include with the data;
replacing, by the server, an express identifier received with the data with a synthetic identifier for association with at least some of the data, wherein the synthetic identifier masks an identity of the wearer from third parties; and
storing, by the server, the data with the determined type of the one or more identifiers, wherein at least some of the data is stored in association with the synthetic identifier.

2. The method of claim 1, further comprising:
determining, in accordance with the at least one identification rule, whether or how the wearer is identified based, at least in part, on a type of the data.

3. The method of claim 1, further comprising:
determining, in accordance with the at least one identification rule, whether or how the wearer is identified based, at least in part, on permitted third-party access to the data.

4. The method of claim 1 further comprising:
associating a first portion of the data with the express identifier that reveals the identity of the wearer based, at least in part, on the identification rule; and
associating a second portion of the data with the synthetic identifier that does not reveal the identity of the wearer based, at least in part, on the identification rule.

5. A method comprising:
receiving, by a server from a wearable device, data related to one or more measurements obtained by the wearable device, wherein the wearable device is mounted to a body surface of a wearer;
receiving, by the server, a selection of at least one permission rule;
determining, by the server, whether third parties can access the data based on the at least one permission rule;
further determining, by the server, a type of data accessible by the third parties determined to have access to the data based on the permission rule;
receiving, by the server, a selection of at least one identification rule;
replacing, by the server, an express identifier received with the data with a synthetic identifier for association with at least some of the data, wherein the synthetic identifier masks an identity of the wearer from the third parties;
determining, by the server, the type of one or more identifiers to include with the data when accessed by the third parties based on the at least one identification rule; and
permitting, by the server, a third party to access the data based on the at least one permission rule and the at least one identification rule.

6. The method of claim 5, further comprising:
determining, according to the at least one permission rule, when the third parties can access the data based, at least in part, on an identity of individual ones of the third parties.

7. The method of claim 5, further comprising:
determining, according to the at least one permission rule, whether third parties can access the data based, at least in part, on a type of third party.

8. The method of claim 5, further comprising:
determining, according to the at least one permission rule, whether third parties can access the data based, at least in part, on a type of intended third-party use of the data.

9. The method of claim 5, further comprising associating at least some of the data with the express identifier based, at least in part, on the at least one identification rule, wherein the express identifier reveals the identity of the wearer.

10. A method, comprising:
receiving, by a server from a wearable device, data related to one or more measurements obtained by the wearable device, wherein the wearable device is configured to be mounted to a body surface of a wearer;
receiving, by the server, a selection by the wearer of at least one rule, wherein the at least one rule comprises an identification rule;
determining, by the server, a type of one or more identifiers associated with the wearer included with the data when accessed by third parties;
receiving, by the server, an express identifier associated with the wearer, wherein the express identifier reveals the identity of the wearer;
replacing, by the server, the express identifier with a synthetic identifier based, at least in part, on the at least the one rule, wherein the synthetic identifier does not reveal the identity of the wearer;
establishing a relationship between the express identifier and the synthetic identifier;
establishing one or more groups based, at least in part, n the at least the one rule; and
storing, by the server, the data from the wearable device, such that the stored data includes an indication that all or part of the data is associated with the one or more groups.

11. The method of claim 10, further comprising:
determining, in accordance with the identification rule, whether or how the wearer is identified based, at least in part, on a type of the data.

12. The method of claim 10, wherein the at least one rule further comprises a permission rule, and further comprising determining whether third parties can access the data.

13. The method of claim 12, further comprising:
determining, in accordance with the permission rule, one or more permitted third-party uses of the data.

14. The method of claim 12, further comprising:
Determining, in accordance with the permission rule, one or more conditions for access to the data by third parties.

* * * * *